United States Patent [19]

Zava et al.

[11] Patent Number: 4,559,820

[45] Date of Patent: Dec. 24, 1985

[54] DEVICE FOR THE CHECKING OF A SPRING FROM A REMOTE LOCATION

[75] Inventors: Francis Zava, Manosque; Louis Coppa, Aix En Provence, both of France

[73] Assignee: Commissariat a l'Energie Atomique, Paris, France

[21] Appl. No.: 501,712

[22] Filed: Jun. 6, 1983

[30] Foreign Application Priority Data

Jun. 14, 1982 [FR] France ................................ 82 10317

[51] Int. Cl.⁴ ............................ G01N 3/26; G01L 1/04
[52] U.S. Cl. ........................................... 73/161; 73/818
[58] Field of Search .................................. 73/161, 4 D

[56] References Cited

U.S. PATENT DOCUMENTS

| | | | |
|---|---|---|---|
| 2,164,453 | 7/1939 | Gaskins | 73/161 |
| 2,296,749 | 9/1942 | Tanner | 33/147 E |
| 2,974,518 | 3/1961 | Jones | 73/1 B |

FOREIGN PATENT DOCUMENTS 2482299 11/1981 France .
0171619 5/1965 U.S.S.R. ................................ 73/161

OTHER PUBLICATIONS

"Testing Valve Springs", Popular Science Monthly, Mar. 7, 1934, p. 68.

Primary Examiner—Daniel M. Yasich
Attorney, Agent, or Firm—Cesari and McKenna

[57] ABSTRACT

A device for the remote checking of the characteristic of a spring includes a system of known masses or weights displaceable in translation in a vertical direction, each of the masses forming said system being vertically displaceable within certain limits with respect to the other masses in such a way that, upon lowering them, their weights are successively supported by the spring and are consequently summated. A dynamometer determines the moment when, during the descent of the system, a given mass rests on the spring. The device then measures the deflection of the spring by measuring the displacement of the mass resting on the spring relative to a reference point fixed with respect to the spring.

11 Claims, 8 Drawing Figures

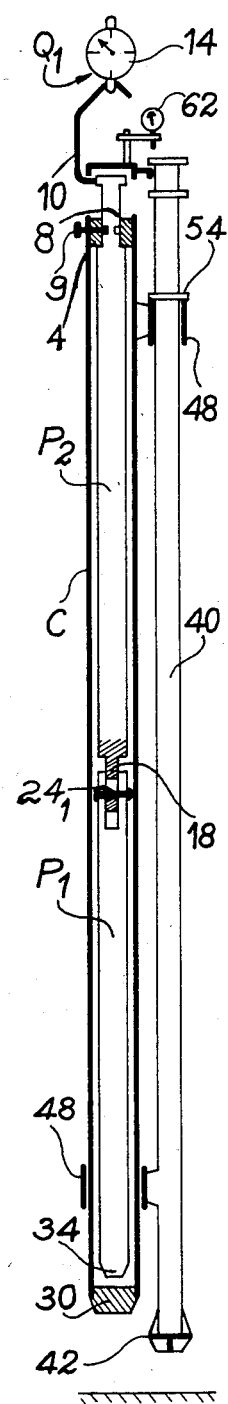
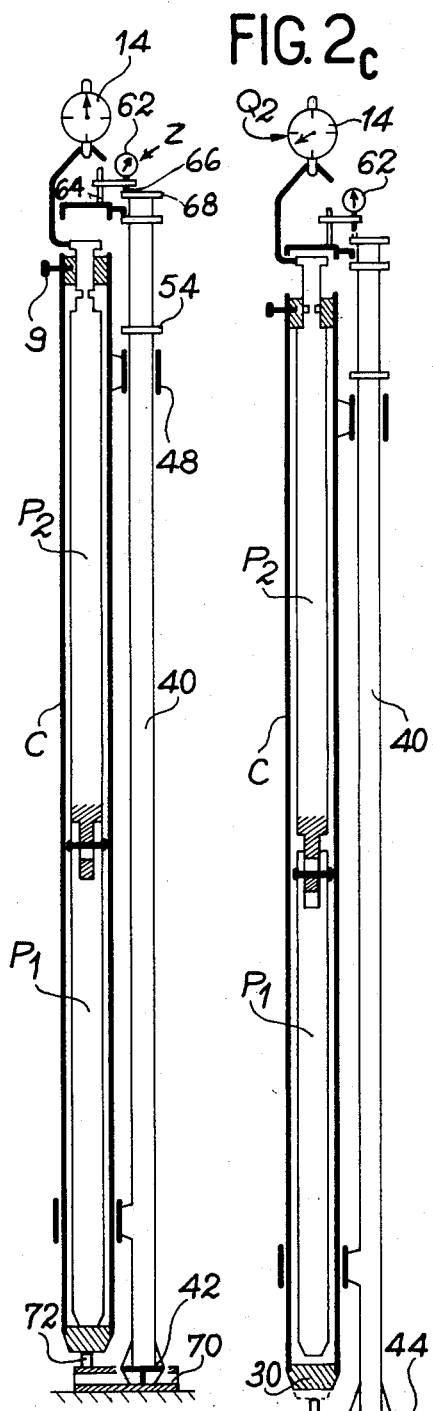
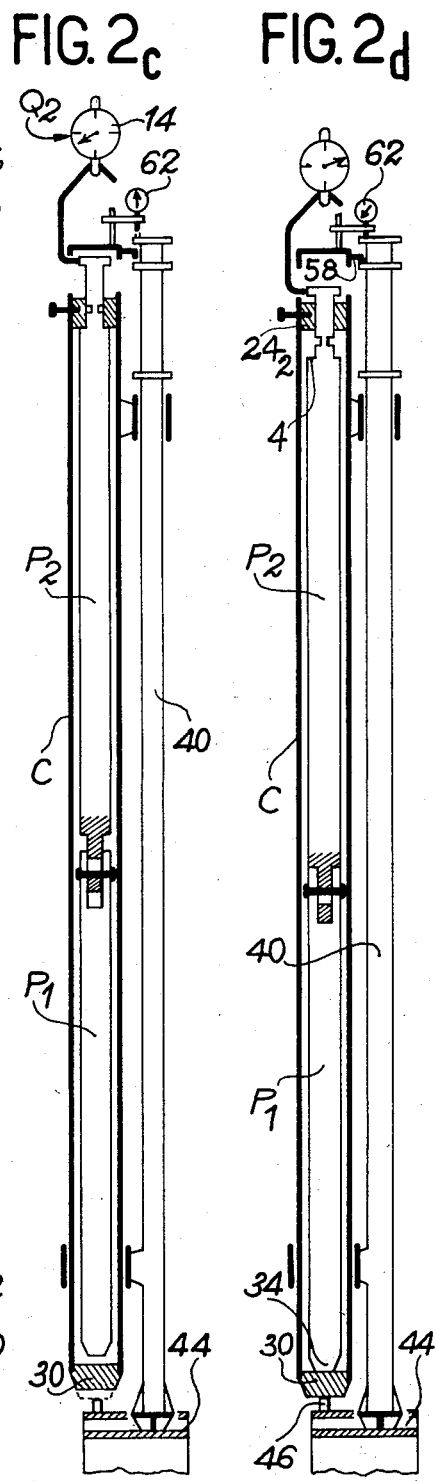
FIG. 2a  FIG. 2b  FIG. 2c  FIG. 2d

4,559,820

DEVICE FOR THE CHECKING OF A SPRING FROM A REMOTE LOCATION

BACKGROUND OF THE INVENTION

The present invention relates to a device for the remote checking of the spring characteristic of a spring, i.e. its characteristic curve of deflection vs. applied load.

A problem of this type occurs when it is difficult or dangerous to approach the spring which requires checking or testing. This is the case, for example, when it is necessary to check the springs of an irradiated nuclear reactor fuel assembly end piece. To prevent the irradiation of personnel, irradiated assemblies are stored in a pond under a minimum water head. Consequently, the springs of the fuel assembly must be checked remotely and under water. The device according to the invention makes it possible to solve this problem.

SUMMARY OF THE INVENTION

The present invention more specifically relates to a device comprising means for applying known loads to the spring and means for measuring the corresponding deflection or camber of the spring under those applied loads. It specifically comprises:

a system of known masses or weights displaceable in translation in a vertical direction, each of the masses forming said system being vertically displaceable within certain limits with respect to the other masses, in such a way that on lowering them, their weights are successively supported by the spring and are consequently summated;

means for determining the moment when, during the descent of the system, a given mass rests on the spring;

the means for measuring the deflection of the spring being constituted by the means for measuring the displacement of the lower mass relative to a reference point fixed with respect to the spring.

Preferably, the means for determining the moment at which a given weight rests on the spring are constituted by a dynamometer integral with a fixing point which is displaceable in translation, the system of masses being suspended on the hook of the dynamometer.

Thus, the dynamometer can be attached to the hook of a pulley block, which makes it possible to progressively lower the system of masses. At the start of the lowering process, the dynamometer indicates the weight of the system of masses. When the lower mass rests on the spring, the reading given by the dynamometer is reduced by the weight of the latter. The corresponding deflection of the spring is then measured.

According to a first variant, the device comprises three masses, respectively: an elongated cylindrical mass, suspended by its upper part on the dynamometer hook and having a shoulder at its upper end;

an also elongated cylindrical mass, positioned beneath the first mass and suspended on the lower part of the latter with an axial clearance;

a column in the form of a hollow cylinder in which are arranged the two aforementioned masses, said column having an inner shoulder, by which it rests on the shoulder of the first-mentioned mass, when the system of masses is suspended.

In order that the weight of the masses rests correctly on the spring to be checked, said masses must be guided vertically in translation. Masses P1 and P2 are guided within the column, which must itself be guided. Preferably, this guidance is brought about by means of a centering column, which rests on a part integral with the fixed end of the spring and by means for guiding the first mentioned column with respect to the centering column.

This latter construction is particularly adapted to the checking of the four springs of a fuel assembly end piece because, by a simple pivoting of the first-mentioned column about the guidance column, it makes it possible to successively check the four springs of the end piece. Preferably, the guidance means are constituted by rings.

The lower end of the column can be closed and in this case the lower mass is constituted by the actual column. In order to measure the deflection of the spring, it is merely necessary to measure the displacement of its upper part, which emerges from the water. Preferably, use is made of a comparator, which measures the displacement of the upper end of the column relative to a fixed reference on the centering column.

According to a variant, the lower end of the column is open and in this case the lower mass is the second-mentioned mass. It is then necessary to check the displacement of this lower mass above the liquid level. A rod, whereof one end is fixed to the lower mass, makes it possible to obtain this result. A comparator measures the displacement of the upper end of the rod relative to a fixed reference on the centering column.

Finally, according to a third variant, the lower end of the column is open and the guidance means of the first and second-mentioned masses are solely constituted by the column itself. During the operation of the device, the column rests on a fixed part integral with one end of the spring. As in the preceding variant, the means for measuring the displacement of the lower mass are constituted by a rod, whereof one end is integral with the second-mentioned mass and by a comparator which measures the displacements of the upper end of the said rod, relative to a fixed reference on the centering column.

The invention also relates to a method for the remote measurement of the characteristics of a spring, wherein it comprises suspending a system of several known masses, each of which can be vertically displaced within certain limits relative to the other masses, the system of masses is progressively lowered, the descent is stopped, when the lower mass rests on the spring, the corresponding dimension of the lower mass is marked with respect to a fixed reference, the progressive lowering of the masses is recommenced, the descent is stopped when a second mass rests on the spring and the corresponding dimension of the lower mass is marked relative to the fixed reference and so on.

BRIEF DESCRIPTION OF THE DRAWINGS

The invention is described in greater detail hereinafter relative to non-limitative embodiments and with reference to the attached drawings, wherein show:

FIGS. 2a to 2d illustrate the operation of the device of FIG. 1.

DETAILED DESCRIPTION OF THE INVENTION

Figure 5:
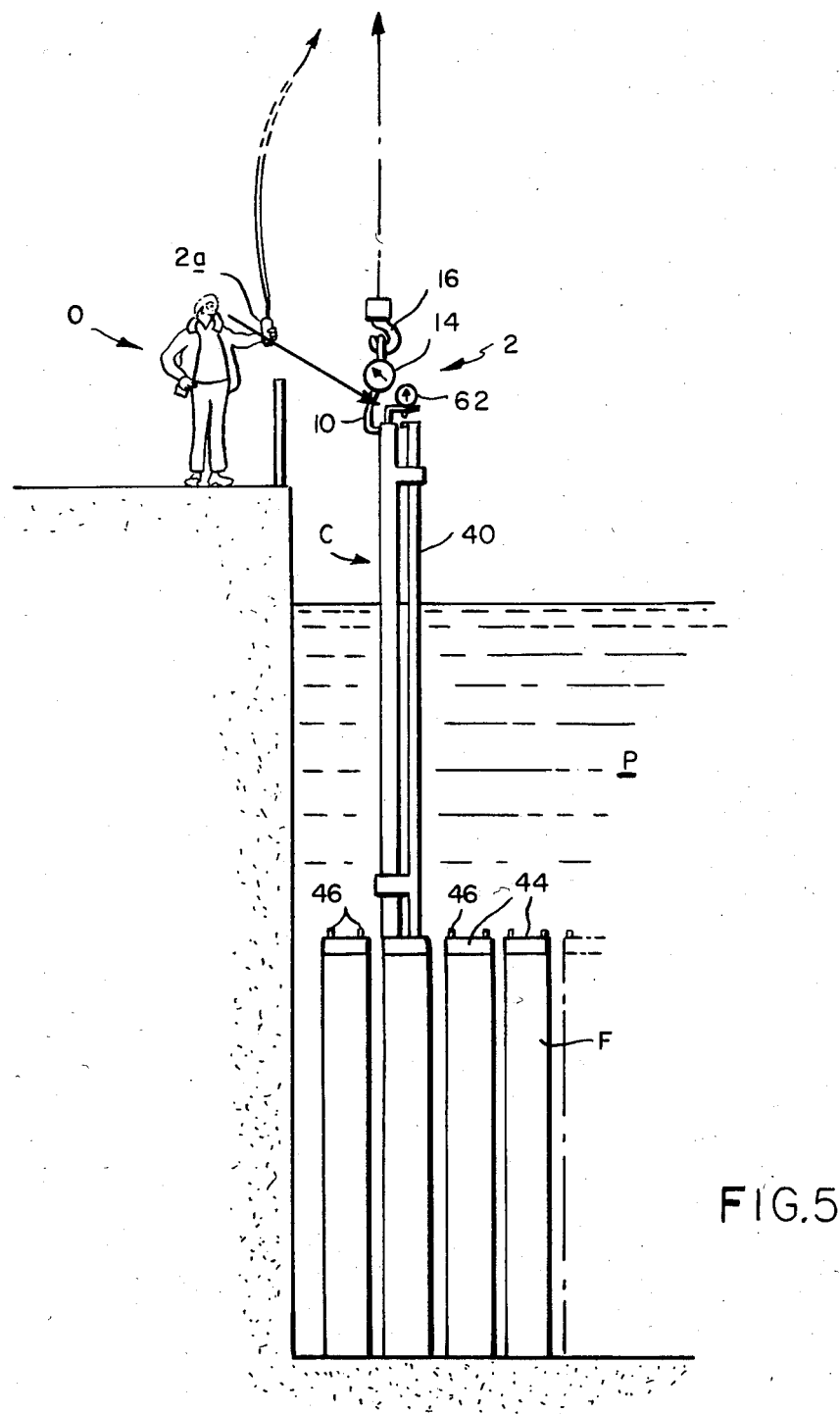
FIG. 5 is a diagrammatic view showing the checking of a nuclear fuel assembly using the FIG. 2 device.

Referring first to FIG. 5, the radioactive fuel assemblies F of a nuclear power plant are invariably submerged at the bottom of a body of water or pond P to protect personnel including an operator O from radiation. Therefore, the operator cannot approach the fuel assembly closer than, say, 4 to 6 meters. However, during the operating life of the assemblies F, it is necessary to inspect them on a routine basis for safety reasons. One such routine inspection involves the checking or measuring of the spring characteristics (i.e. deflection vs. load) of the springs 46 customarily mounted to the upper end pieces 44 of assemblies F and which resiliently engage the bottom plate of the reactor core (not shown) when the reactor is in operation. Since the assemblies must remain immersed in pond P, the operator must take these measurements from a remote location at the edge of the pond as shown in FIG. 5. FIGS. 2 and 5 illustrate a device shown generally at 2 for enabling operator O to do that. As seen there, device 2 comprises three moving masses, namely a mass P1, a mass P2 and column C. Each of the masses P1 and P2 is in the form of an elongated cylinder. In its upper part, mass P2 has a shoulder 4 and is surmounted by a smaller diameter portion 6, in which there is a circular groove 8. Portion 6 is fixed to a handlng ring 10, which is itself attached to the hook 12 of a dynamometer 14. Dynamometer 14 is suspended on the hook 16 of a not shown lifting means, such as a pulley block controlled by hand controller 2a. A locking finger 9 makes it possible to lock column C during the displacement of the system.

In its lower part, mass P2 has a lug 18, in which is provided an oblong hole 20. Lug 18 enters a fork 22, made in the upper part of mass P1. A clearance enables the two parts to slide. A pin $24_1$, integral with the fork of mass P1, traverses the oblong hole 20. Thus, mass P1 is suspended on mass P2, whilst being able to slide relative to the latter with a certain deflection limited by the length of oblong hole 20. Masses P1 and P2 are disposed within a column C in the form of a hollow cylinder.

Figure 1:
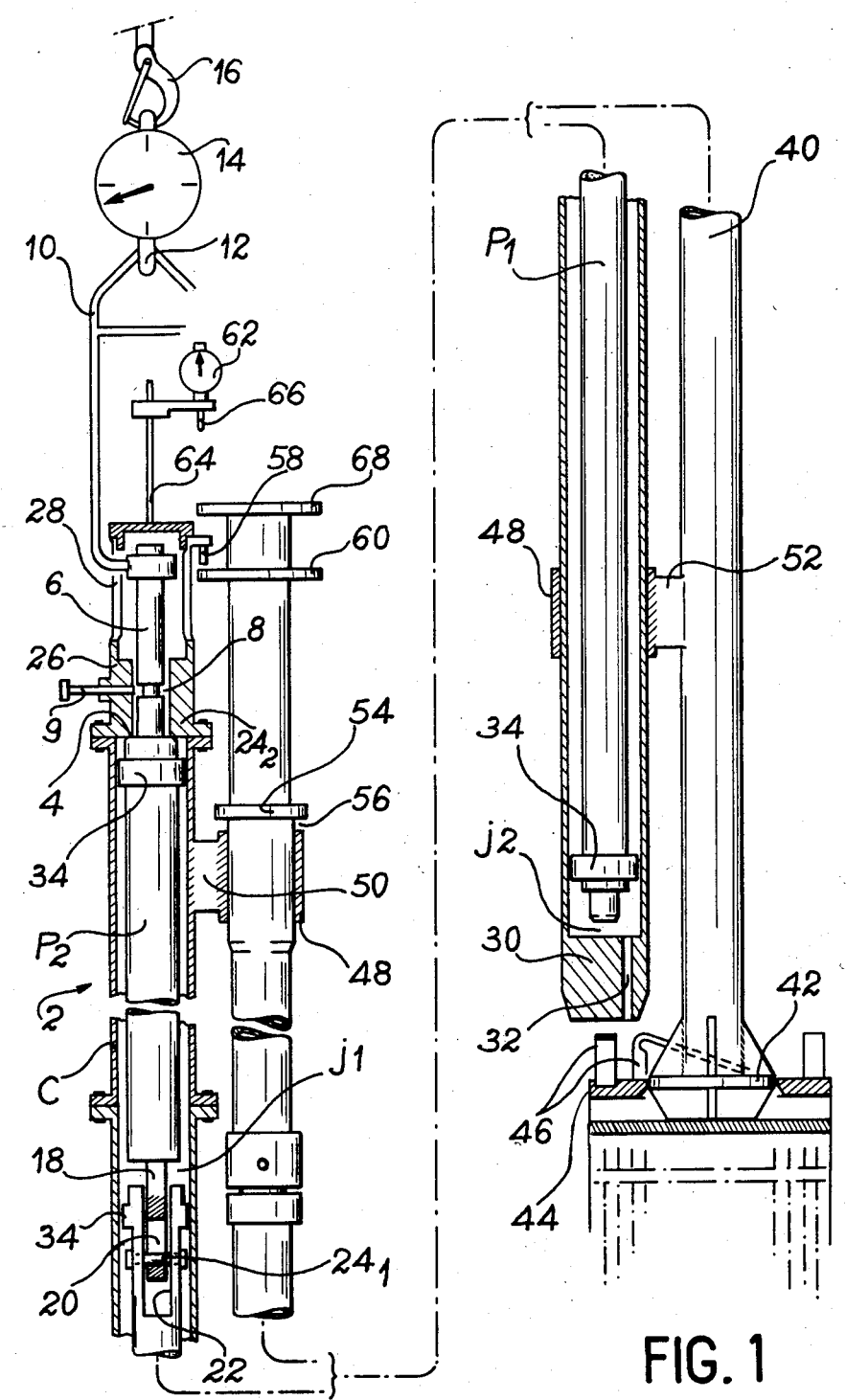
FIG. 1 a first embodiment of a spring checking device according to the invention.

Column C has an inner shoulder $24_2$ in its upper part. In order to permit the introduction of masses P1 and P2, it was necessary therefore in the present embodiment to construct the column C in the form of several dismantlable parts. As can be seen in FIG. 1, shoulder $24_2$ is obtained by means of a head 26, fixed in any appropriate way to column C. Head 26 is hollow in order to receive portion 6 of mass P2. On either side, it has large openings 28, which permit the passage of handling ring 10.

When the system of the device is suspended on handling ring 10, column C rests on shoulder 4 via shoulder $24_2$. In this position, there is a clearance $j_1$ between masses P1 and P2 and a clearance $j_2$ between the lower end of mass P1 and the bottom 30 of column C. A pipe 32 in bottom 30 links the interior and the exterior of column C. This pipe enables water to penetrate the interior of the column, when the device is immersed in the water of the storage pond for the assemblies.

Masses P1 and P2 can be displaced in translation within column C with a deflection given by the construction of the device and in particular by the value of clearances $j_1$ and $j_2$. Guide rings 34 made on masses P1 and P2 ensure the guidance of these masses during their translation.

Figure 3:
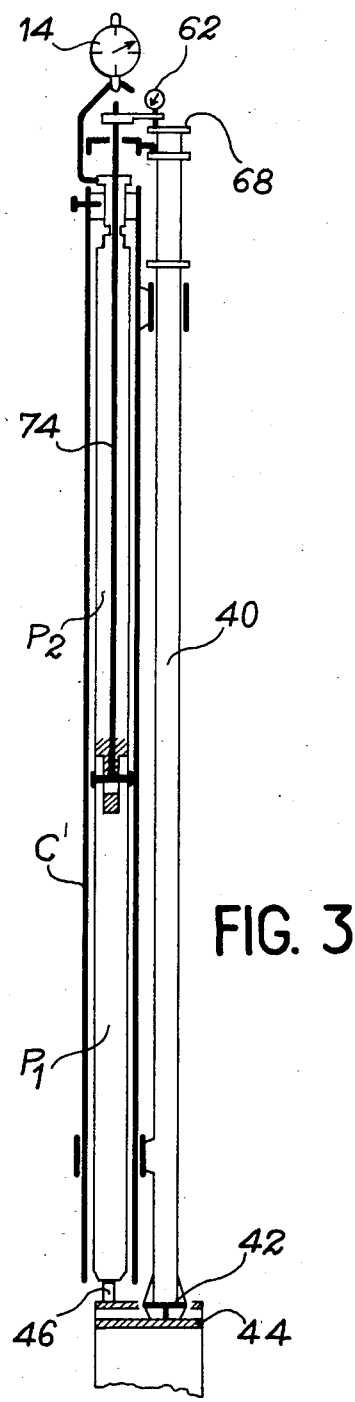
FIG. 3 a second embodiment according to the invention.

The device shown in FIGS. 1 to 3 also has a guidance column 40, provided with a leg 42, which bears on the upper end piece 44 of a fuel assembly diagrammatically shown in FIG. 1 which is grounded. The upper end piece 44 has four identical springs 46, whereof only three can be seen in the drawing. One of the springs is shown in profile, whilst the other two are shown in end view. Each spring 46 is fixed by one of its ends to the upper end piece 44. Its other end is guided in the upper end piece. The function of these springs is, in per se known manner, the application of the fuel assembly to the lower plate of the core during the operation of the reactor. The device according to the invention makes it possible to check the characteristics of each of these springs.

Two guidance rings 48 guide column C relative to guidance column 40. A rib 50 joins the upper ring 48 to column C. A rib 52 connects the lower ring 48 to guidance column 40. In addition, the upper ring 48 permits the suspension of column 40. To this end, column 40 has a collar 54 against which the upper ring 48 comes into contact when the system is suspended. In the position shown in FIG. 1, leg 42 rests on the upper end piece and column C is shown in a slightly lowered position, which defines a clearance 56 between ring 48 and collar 54. However, in this position, bottom 30 of column C does not yet rest on a spring 46, as can be gathered from the drawing.

There is also a pointer 58 on head 26. Pointer 58 can penetrate the interior of a not shown positioning orifice, made in collar 60, when column C is flush with a spring 46. Collar 60 has four identical orifices, distributed every 90° over collar 60 and corresponding to each of the four springs 46. In the position shown in FIG. 1, pointer 58 has not yet engaged with the interior of the positioning orifice.

A comparator 62, mounted on a rod 64, integral with head 26, makes it possible to measure the relative displacement of column C with respect to the guidance column 40. For this purpose, the support of the comparator is slid along rod 64 until its point 66 comes into contact with the end of column 40, which is terminated by a plate 68.

A description will now be given with reference to FIGS. 2a to 2d of the operation of the device shown in FIG. 1.

In FIG. 2a, the device according to the invention is suspended on the handling ring 10, whilst column C rests on shoulder 4 of mass P2. The guidance tubular column 40 is suspended on ring 48 by collar 54. Mass P1 is held on mass P2 by pin $24_1$. It can be seen that mass P1, column C and guidance column 40 are all suspended on mass P2, which is itself fixed to the handling ring. Dynamometer 14 indicates a load $Q_1$ equal to the weight of the system of the device. The locking finger 9 is inserted in groove 8.

Referring now to FIG. 2b, prior to checking a spring 46, column 40 is rested on a control box 70 which is geometrically similar to the upper end piece 44. Box 70 has a false spring 72 which is actually a rigid part whose height is equal to the free height of a new or undeflected and undeformed spring 46. Using this false spring, it is possible to calibrate comparator 62. To do this, the comparator is slid down on rod 64 until its end 66 is applied to plate 68 and then locked in position. An arbitrary reading z on the comparator is then plotted, which makes it possible to subsequently determine the ordinate at the origin of each of the spring 46 and to say whether these springs do or do not have a permanent deformation. During such calibration step, dynamometer 14 indicates a zero load, because the device column rests on control box 70.

After the operation of calibrating the comparator has been completed, the device is placed above the upper end piece 44 (FIG. 2c). The guidance column 40 rests on said end piece 44. Masses P1 and P2 and column C are suspended on the hook of dynamometer 14. The latter indicates a load $Q_2$ equal to the weight in water of these three masses because, as has been stated hereinbefore, the irradiated fuel assembly is immersed under a certain head of water. The height of the device exceeds this head of water, in such a way that the measuring means are not immersed. Starting from the position shown in FIG. 2c, the fixing point of the dynamometer is progressively lowered, e.g. by means of a not shown chain pulley block. A first swing of the comparator needle indicates the moment at which the bottom 30 of column C enters in contact with the spring 46 to be checked as shown in dotted lines in FIG. 2c. At this moment, there is a theoretical contact between column C and the spring, i.e. the mass of column C does not yet rest on this spring. Thus, the dynamometer reading is substantially the same as in the stage shown in solid lines in FIG. 2c, on neglecting the hydrostatic buoyancy corresponding to the volume of water displaced by the lowering of column C from the first position of FIG. 2c to the theoretical contact position shown in dotted lines.

The dimension x of the comparator is plotted. The permanent deformation of the spring from the ideal spring height of false spring 72 is given by the difference $z-x$. This value corresponds to the ordinate at the origin of the characteristic of the spring.

The fixing point of the dynamometer 14 continues to be lowered by means of the chain pulley block. The descent is stopped, when the dynamometer indicates a value equal to $Q_2$, reduced by the known mass of column C. In this position, the weight of the column rests on spring 46. Conversely, masses P1 and P2 remain suspended on the handling ring 10. Thus, a clearance appears between shoulder 4 of mass P2 and shoulder $24_2$ of column C. However, there is still no contact between the lower end of mass P1 and the bottom 30 of column C. In other words, the clearance $j_1$ shown in FIG. 1 has not yet been cancelled.

Under the effect of the weight of column C, spring 46 deflects and comparator 62 supplies a reading y. Thus, if the mass of column, C is e.g. 50 kg, the difference $y-z$ gives the deflection of the spring under a load of 50 kg. This gives a second point of the characteristic of the spring.

The device described also makes it possible to obtain two other points, which correspond to the application of masses P1 and P2 to the spring.

The fixing point of the dynamometer 14 is further slowly lowered until it indicates that its load has been reduced by the weight of mass P1, which is then applied to the spring. The lower portion of mass P1 comes into contact with the bottom 30 of column C. In this position, its weight is transmitted to spring 46. The corresponding reading z of the comparator is plotted, which makes it possible to obtain, as hereinbefore, a third point of the characteristic giving the true deflection of the spring under a load equal to the weight of column C and weight P1.

On continuing to lower the fixing point of the dynamometer, one arrives at the position shown in FIG. 2d, in which the masses P1 and P2 and the mass of column C rest on spring 46. A fourth reading of comparator 62 is then plotted, which makes it possibe to establish a fourth point of the characteristic of the spring.

Each of the three other springs of the upper end piece 44 is successively checked by the successive 90° rotation of column C around guidance column 40. On each occasion, pointer 58 makes it possible to lock column C in a correct angular orientation. It should be noted that in order to check the three other springs, it is not necessary to repeat stage 2b corresponding to the calibration of comparator 62.

FIG. 3 shows a second embodiment of the invention, which essentially differs from that of FIGS. 1 and 2 in that the lower part of column C' is open. Thus, the mass of the column cannot rest on spring 46. Thus, there are only two masses, namely P1 and P2, for establishing the characteristic of the spring, which is however adequate, because they permit the plotting of three points thereof. The first point corresponds to the ordinate at the origin of spring 46. It is obtained, in the manner described relative to FIGS. 2a to 2d, by the reading of comparator 62 at the time of theoretical contact between mass P1 and spring 46. A second point is obtained when mass P1 rests on the spring and a third when masses P1 and P2 rest on the spring.

Column C' does not function as the lower mass, i.e. that which first comes into contact with the spring. In this embodiment, the lower mass is constituted by P1. In view of the fact that for measuring the deflection of the spring, it is necessary to measure the displacement of this lower mass, a rod 74 is fixed to pin $24_1$. Rod 74 passes into the interior of mass P2 and can freely slide therein. Thus, rod 74 indicates the displacements of mass P1 and makes it possible to raise said reading above the level of the water. Thus, the support of comparator 62 is fixed to the upper part of rod 74.

However, with respect to the fixed reference point integral with the fixed end of the spring, there is no difference compared with the previous embodiment. This reference point is here again constituted by plate 68 of guidance column 40.

Figure 4:
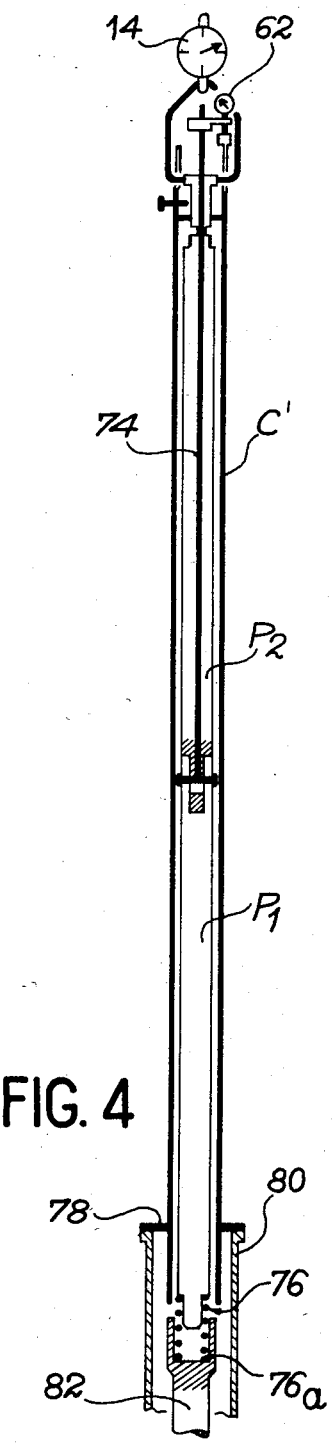
FIG. 4 a third embodiment of the invention.

FIG. 4 shows a third embodiment of the invention, which is adapted to the checking of a spring, like helical spring 76.

The device of FIG. 4, like that of FIG. 3, only has the two masses P1 and P2, making it possible to obtain three points of the characteristic of the spring 76.

Guidance column 40 of FIGS. 1, 2a-2d and 3 serves no useful purpose in this embodiment because it is not necessary for successively checking several springs. Masses P1 and P2 are guided by column C', which is fixed during the measurements. It is also column C' which supplies a fixed reference point integral with the lower end 76a of the helical spring. To this end, column C' has an external collar 78, which bears on cylinder 80, which is itself fixed with respect to the bearing base 82 of spring 76. Column C' guides the two masses P1 and P2 during their vertical displacement.

As in the embodiment of FIG. 3, a rod 74 integral with mass P1 makes it possible to raise the displacement of said mass and consequently follow the deflection of the spring, by means of comparator 62.

What is claimed is:

1. A device for the measurement from a remote location of the characteristic of a spring of the type having a fixed portion and deflectable portion, said device having means for applying known loads to said deflectable portion of the spring and means for measuring the corresponding deflection thereof, in which the means for applying the known loads are constituted by:
- a series of known masses displaceable vertically, each of the masses forming said series being loosely linked to the other masses of the series and movable relative to one another so that, upon lowering them, said masses are successively supported by the spring;
- means for determining when, during the descent of said series of masses, each mass of said series of masses rests on said deflectable portion of the spring;
- the means for measuring the deflection of the spring are constituted by the means for indicating to said remote location the displacement of the mass then resting on the deflectable portion of the spring relative to a reference point fixed with respect to said fixed portion of the spring, wherein the means for determining when a mass of said series of masses rests on the spring are constituted by a vertically displaceable dynamometer that provides an indication to said remote location, the system of masses being suspended on the hook of the dynamometer; and wherein said series of masses is comprised of three masses, respectively:
- a first elongated mass suspended by its upper part on the dynamometer and having a shoulder at its upper end;
- a second elongated mass positioned beneath the first mass and suspended on the lower part of the latter with an axial clearance; and
- a third mass formed as a hollow tubular column in which are arranged said first and second masses, said hollow tubular column having upper and lower ends and an inner shoulder, by which it rests on the shoulder of the first mass, when the series of masses is suspended.

2. A device according to claim 1 wherein there are two said weights namely:
- a first elongated weight suspended by its upper part on the indicating means and having a shoulder at its upper end; and
- a second elongated weight positioned beneath the first weight and suspended on the lower part of the latter with axial clearance;
- there is also an elongated column in the form of a hollow cylinder in which are arranged said first and second masses, said hollow tubular column having an inner shoulder by which it rests on the shoulder of the first weight when the plurality of weights is suspended;
- it has also guidance means constituted by a centering column which bears on a part integral with the fixed portion of the spring and by means for guiding said hollow tubular column relative to said centering column; and
- said hollow tubular column is open at its lower end and the means for guiding the weights are constituted by said hollow tubular column which, during the operation of the device, rests on a fixed part integral with the fixed portion of the spring, the means for displaying being constituted by a rod having upper and lower ends, and whose said lower end is fixed to the lower mass and by a comparator, which measures the displacement of the upper end of the rod with respect to a fixed reference on the tubular column.

3. A device according to claim 1, wherein the lower mass is linked to the upper mass by a pin having two ends, said ends being fixed to the lower mass and sliding in an oblong hole in the upper mass.

4. A device according to claim 1, wherein it has guidance means constituted by a centering column, which bears on a part integral with the fixed end of the spring and by means for guiding said hollow tubular column relative to said centering column.

5. A device according to claim 4, wherein the means for guiding said hollow tubular column relative to the centering column are constituted by rings.

6. A device according to claim 4, wherein said hollow tubular column is closed at its lower end and the means for indicating the displacement of the lower mass are constituted by a comparator, which measures the displacement of the upper end of the said hollow tubular column wth respect to a fixed reference on the centering column.

7. A device according to claim 2 wherein there are two said weights namely:
- a first elongated weight suspended by its upper part on the indicating means and having a shoulder at its upper end; and
- a second elongated weight positioned beneath the first weight and suspended on the lower part of the latter with axial clearance;
- there is also an elongated column in the form of a hollow cylinder in which are arranged said first and second masses, said hollow tubular column having an inner shoulder by which it rests on the shoulder of the first weight when the plurality of weights is suspended;
- it has also guidance means constituted by a centering column which bears on a part integral with the fixed portion of the spring and by means for guiding said hollow tubular column relative to said centering column; and
- the lower end of said hollow tubular column is open and the means for displacing are constituted by a rod having upper and lower ends, and whose said lower end is fixed to the lower weight and by a comparator, which measures the displacement of the upper end of the rod relative to a fixed reference on the centering column.

8. A device for the measurement from a remote location of the spring characteristic of a spring of the type having a fixed portion and a deflectable portion, said device comprising:
- a plurality of known weights;
- means for loosely linking said weights in a vertical series so that each weight is movable to a limited extent vertically relative to any adjacent weight in the series;
- means to facilitate lowering said weight series onto the deflectable portion of a spring so that said weights are supported one after the other in upward succession by the spring;
- means defining a reference position;
- means for indicating to said remote location the vertical displacement from said reference position of the weight series when each weight of the series first begins to be applied to the spring; and
- means for displaying to said remote location the sum of the weights of the series above said each weight and not yet applied to the spring at each indication of the indicating means so that as said weight series is lowered onto the spring, the indicating and display means together enable one at said remote location to determine each successive vertical deflection of the spring caused by the application of each successive known weight of the weight series to the spring.

9. The device according to claim 8 wherein the displaying means are comprised of a dynamometer from which the weight series is suspended.

10. The device according to claim 8 wherein the indicating means are comprised of means for measuring the vertical displacement of the lowest weight of the weight series relative to the fixed portion of the spring.

11. The device according to claim 10 and further including means for calibrating the indicating means to account for any permanent initial deformity in the spring being measured by the device.

* * * * *